United States Patent
Grodzki (10) Patent No.: US 9,523,755 B2
(45) Date of Patent: Dec. 20, 2016

(54) METHOD AND MAGNETIC RESONANCE APPARATUS FOR NON-SELECTIVE EXCITATION OF NUCLEAR SPIN SIGNALS IN AN EXAMINATION SUBJECT

(71) Applicant: David Grodzki, Erlangen (DE)

(72) Inventor: David Grodzki, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 1036 days.

(21) Appl. No.: 13/630,232

(22) Filed: Sep. 28, 2012

(65) Prior Publication Data

US 2013/0082704 A1   Apr. 4, 2013

(30) Foreign Application Priority Data

Sep. 30, 2011 (DE) .................. 10 2011 083 871

(51) Int. Cl.
*G01R 33/565* (2006.01)
*A61B 5/055* (2006.01)
*G01R 33/48* (2006.01)

(52) U.S. Cl.
CPC .......... *G01R 33/5659* (2013.01); *A61B 5/055* (2013.01); *G01R 33/482* (2013.01); *G01R 33/4816* (2013.01); *G01R 33/4824* (2013.01)

(58) Field of Classification Search
CPC .......... G01R 33/5659; G01R 33/4816; G01R 33/4824; G01R 33/482; A61B 5/055
See application file for complete search history.

(56) References Cited

U.S. PATENT DOCUMENTS

| 6,078,175 | A | * | 6/2000 | Foo | G01R 33/56341 |
| | | | | | 324/300 |
| 6,946,839 | B2 | * | 9/2005 | Porter | G01R 33/5615 |
| | | | | | 324/307 |
| 7,038,453 | B2 | * | 5/2006 | Feiweier | G01R 33/583 |
| | | | | | 324/309 |
| 7,292,039 | B1 | * | 11/2007 | Laub | G01R 33/4828 |
| | | | | | 324/309 |

(Continued)

OTHER PUBLICATIONS

Idiyatullin et al.: "Fast and quiet MRI using a swept radiofrequency", in J. Magn. Reson., vol. 181, (2006) pp. 342-349; Magazine.

(Continued)

*Primary Examiner* — Dixomara Vargas
(74) *Attorney, Agent, or Firm* — Schiff Hardin LLP (57) ABSTRACT

In a method for non-selective excitation of nuclear spin signals in an examination subject with a magnetic resonance system, RF excitation pulses are radiated to excite nuclear spin signals in the examination subject with simultaneous switching of gradients for spatial coding of the excited nuclear spin signals, wherein the RF excitation pulses are designed such that the base frequency of a radiated RF excitation pulse is adapted to the simultaneously switched gradient. By the dynamic adaptation of the radiated RF excitation pulses to the respective simultaneously switched gradients, artifacts due to insufficiently excited nuclear spins in an examination region to be examined (in particular even in examination regions that are arranged off-center) are avoided.

14 Claims, 4 Drawing Sheets

(56) References Cited

U.S. PATENT DOCUMENTS

| | | | | |
|---|---|---|---|---|
| 8,498,688 B2* | 7/2013 | Lamerichs | ............ | G01R 33/485 600/407 |
| 8,749,233 B2* | 6/2014 | Littmann | ............... | A61B 5/055 324/307 |
| 8,803,522 B2* | 8/2014 | Paul | ....................... | A61B 5/055 324/309 |
| 8,873,820 B2* | 10/2014 | Grodzki | ............. | G01R 33/4816 382/128 |
| 8,878,533 B2* | 11/2014 | Grodzki | ................ | A61B 5/055 324/307 |
| 9,097,776 B2* | 8/2015 | Grodzki | ............. | G01R 33/4816 |
| 9,151,816 B2* | 10/2015 | Fautz | ............... | G01R 33/56545 |
| 9,170,314 B2* | 10/2015 | Li | ...................... | G01R 33/4833 |
| 9,320,454 B2* | 4/2016 | Grodzki | ................ | A61B 5/062 |
| 9,395,429 B2* | 7/2016 | Grodzki | ............. | G01R 33/4816 |
| 2004/0061496 A1* | 4/2004 | Ookawa | ........................ | 324/307 |
| 2006/0022675 A1* | 2/2006 | Blank et al. | .................. | 324/316 |
| 2006/0173277 A1 | 8/2006 | Elgort et al. | | |
| 2010/0241389 A1 | 9/2010 | Griswold et al. | | |

OTHER PUBLICATIONS

Nielles-Vallespin et al: "3D Radial Projection Technique With Ultrashort Echo Times for Sodium MRI: Clinical Applications in Human Brain and Skeletal Muscle", Magnetic Resonance in Medicine vol. 57, (2007) pp. 74-81.

Heid at al., "Rapid Single Point (RASP) Imaging", SMR, 3rd Annual Meeting, (1995) p. 684.

\* cited by examiner

METHOD AND MAGNETIC RESONANCE APPARATUS FOR NON-SELECTIVE EXCITATION OF NUCLEAR SPIN SIGNALS IN AN EXAMINATION SUBJECT

BACKGROUND OF THE INVENTION

Field of the Invention

The invention concerns a method for non-selective excitation of nuclear spin signals in an examination subject, as well as a magnetic resonance system, a non-transitory, computer-readable data storage medium encoded with programming instructions to implement such a method.

Description of the Prior Art

Magnetic resonance (MR) is a known modality with which images of the inside of an examination subject can be generated. Expressed simply, for this purpose the examination subject is positioned within a strong, static, homogeneous basic magnetic field (also called a $B_0$ field) with field strengths of 0.2 Tesla to 7 Tesla and more, such that the nuclear spins of the examination subject orient along the basic magnetic field. To trigger magnetic resonance signals, radio-frequency excitation pulses (RF pulses) are radiated into the examination subject, the triggered nuclear magnetic resonance signals are measured, and MR images are reconstructed or spectroscopy data are determined based on these nuclear magnetic resonance signals. For spatial coding of the measurement data, rapidly switched magnetic gradient fields (called "gradients" for short) are superimposed on the basic magnetic field. The acquired measurement data are digitized and stored as complex numerical values in a k-space matrix. An associated MR image can be reconstructed from the k-space matrix populated with such values, for example by means of a multidimensional Fourier transformation.

In the triggering of the magnetic resonance signals, the spins located in the examination region are excited out of their rest state and (from a classical consideration) tipped or flipped into the transverse plane. This transverse magnetization can be measured by induction.

In the excitation, a distinction can be made between selective RF excitation pulses (that, for example, only excite one slice in the examination subject) and non-selective RF excitation pulses. Non-selective RF excitation pulses optimally uniformly excite the entire examination subject, or at least the examination region to be examined in the examination subject. Additional gradients are switched for spatial resolution. For example, for a resolution in the slice direction, gradients are switched in the slice direction.

MR sequences are known that can use non-selective RF excitation pulses. For example, the known RASP sequence as described by Heid and Deimling in "Rapid Signal Point (RASP) Imaging", SMR, 3rd Annual Meeting, Page 684, 1995. Additional examples are, for example, turbo spin echo sequences or even what is known as the UTE ("Ultrashort Echo Time") sequence, for example as described in the article by Sonia Nielles-Vallespin, "3D radial projection technique with ultrashort echo times for sodium MRI: Clinical applications in human brain and skeletal muscle", Magn. Res. Med. 2007; 57; P. 74-81.

In some of these sequences, different gradients are already switched at the point in time of the excitation in order to make the measurement as quiet as possible, i.e. to minimize noise development due to the gradient switchings. In order to ensure a uniform excitation of the examination subject, the spectral bandwidth of the RF excitation pulse that is used must be relatively high, and the duration of the RF excitation pulse must be as short as possible.

If the spectral width of the non-selective RF excitation pulse is not sufficient in order to excite all spins in the examination subject at every gradient switching, in defined gradient configurations the outer regions of the examination region to be imaged are not excited, or are excited only to a limited extent. This leads to a blurring of the affected regions of the examination region in the MR images reconstructed from the measurement data. For measurements of examination regions whose center does not coincide with the isocenter of the magnetic resonance system (thus with the center of the measurement volume of the magnetic resonance system), such blurring artifacts increase due to the absence of excitation via the RF excitation pulse. Such measurements at examination regions to the side of the isocenter—for example measurements of the hand or the elbow (among other things) of a patient—are also designated as "off-center measurements".

This problem has previously been ignored, for the most part. At best, the strength of the gradients is reduced. However, imaging-relevant variables such as the readout bandwidth, the repetition time TR and the contrast of the image change with this. An expansion of the spectral excitation width of an RF excitation pulse by reducing the duration of the RF excitation pulse simultaneously reduces the maximum achievable excitation flip angle and the precision of the actually emitted RF excitation pulse proportional to the duration of the RF excitation pulse, and therefore likewise is limited in its application.

SUMMARY OF THE INVENTION

An object of the present invention is to provide a method for non-selective excitation of nuclear spin signals in an examination subject with a magnetic resonance apparatus and a non-transitory storage medium to implement such a method, which enable a sufficient excitation of the nuclear spins in the examination region even given off-center measurements.

In a method according to the invention for non-selective excitation of nuclear spin signals in an examination subject by means of a magnetic resonance apparatus, RF excitation pulses for excitation of nuclear spin signals in the subject are radiated into the examination subject with simultaneous switching of gradients for spatial coding of the excited nuclear spin signals, with the RF excitation pulses designed such that the base frequency of a radiated RF excitation pulse is adapted to the simultaneously switched gradients.

By the dynamic adaptation of the radiated RF excitation pulses to the respective simultaneously switched gradients, artifacts due to insufficiently excited nuclear spins in an examination region to be examined are avoided, in particular even in examination regions that are arranged off center. Rather, with the method according to the invention a uniform excitation of all nuclear spins in the examination region is achieved. It is thus not necessary to vary either the duration of the RF excitation pulses or the gradients relative to conventional measurements. Customary measurement parameters can therefore be used, and consistent image contrasts can be achieved. Such an adaptation to simultaneously switched gradients can be implemented, for example, in connection with a RASP sequence.

In an exemplary embodiment, the base frequency of an RF excitation pulse is adapted such that this base frequency corresponds to the Larmor frequency present (due to the switched gradients) at the examination region of the examination subject. In this way it is ensured that the nuclear spins in the examination region to be examined are actually excited.

A magnetic resonance apparatus according to the invention has a basic field magnet, a gradient field system, a radio-frequency antenna, and a control device to control the gradient field system and the radio-frequency antenna, to receive measurement signals acquired by the radio-frequency antenna, to evaluate the measurement signals, and to create magnetic resonance images, designed to implement the method described herein.

The above object also is achieved in accordance with the present invention by a non-transitory, computer-readable data storage medium encoded with programming instructions that, when the storage medium is loaded into a computerized control and evaluation system of a magnetic resonance apparatus, cause the magnetic resonance apparatus to be operated in order to implement one or more of the above-described embodiments of the inventive method.

The magnetic resonance apparatus and the data storage medium achieve advantages comparable to those described above in connection with the embodiments of the method.

DESCRIPTION OF THE PREFERRED EMBODIMENTS

Figure 1:
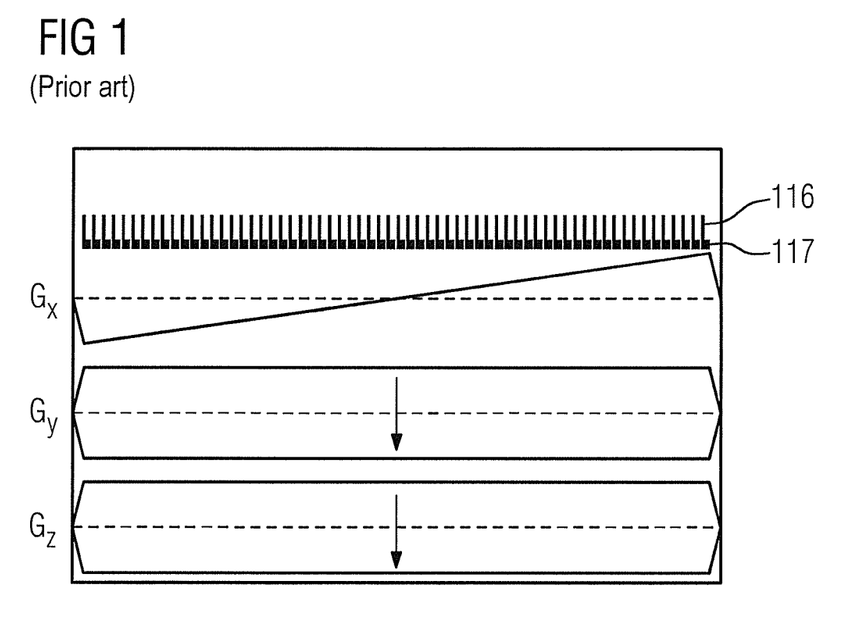
FIGS. 1 and 2 illustrate the known RASP method.

A known sequence to acquire a line in k-space is shown in FIG. 1. It is apparent that the two phase coding gradients $G_y$ and $G_z$ are activated with a constant strength, while the strength of the third phase coding gradient $G_x$ increases continuously.

Figure 2:
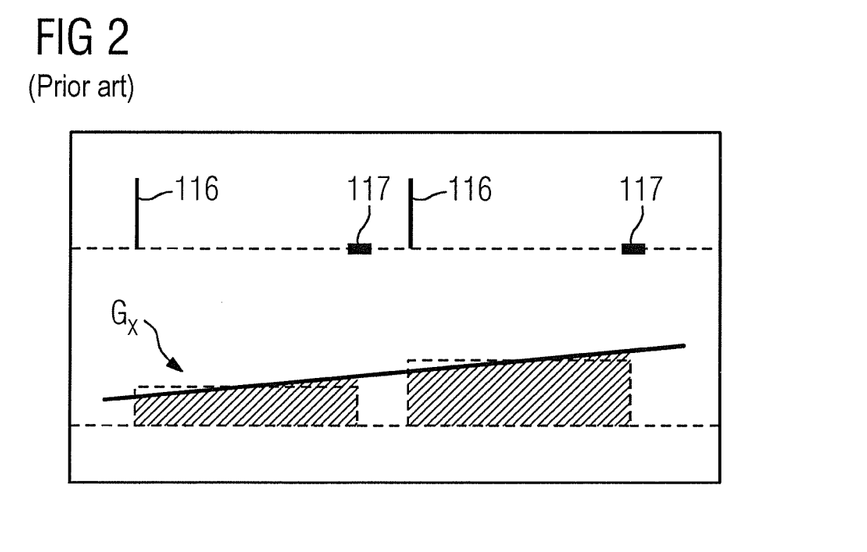

The acquisition of two raw data points according to FIG. 1 is presented in detail in FIG. 2. It is apparent that the echo time—i.e. the time interval from the RF excitation pulse 116 up to the beginning of the readout time period 117 is constant. Moreover, the phase coding gradient $G_x$ travels in stages from bottom to top. The phase coding gradient $G_x$ to read out a raw data point is thereby held constant, which means that the phase coding gradient $G_x$ is held constant for the time period TE (echo time).

According to the invention, the base frequency of the radiated RF excitation pulses 116 is adapted to the respective simultaneously switched gradients $G_x$, $G_y$, $G_z$. This means that the base frequency of each RF excitation pulse radiated in the sequence that is used is dynamically changed in the course of the sequence for each RF excitation pulse, as is further described in detail with regard to FIG. 5.

Figure 3:
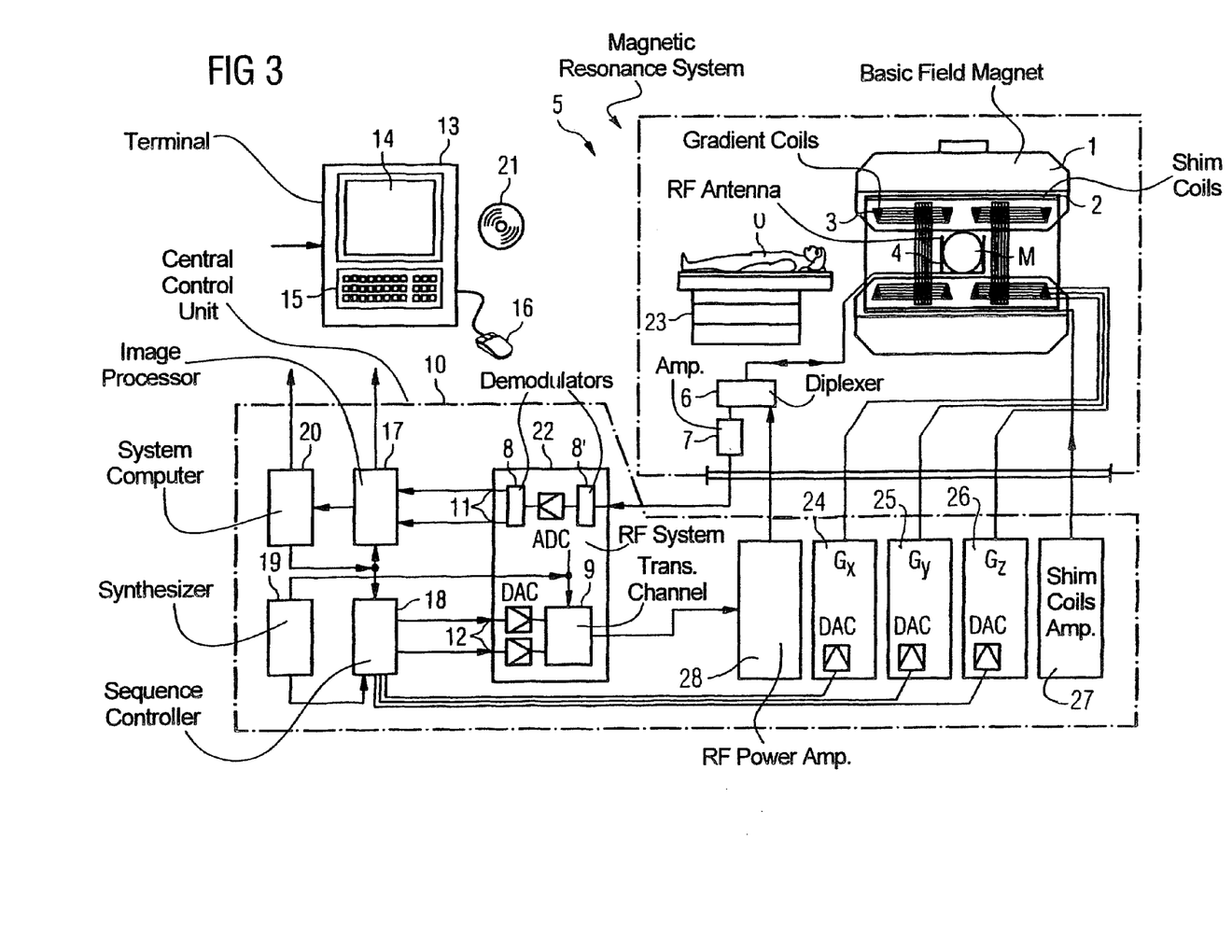
FIG. 3 schematically illustrates a magnetic resonance system according to the invention.

FIG. 3 schematically illustrates a magnetic resonance system 5 (a magnetic resonance imaging or tomography apparatus). A basic field magnet 1 generates a temporally constant, strong magnetic field for polarization or alignment of the nuclear spins in an examination region of an examination subject U, for example of a part of a human body that is to be examined, who lies on a table 23 and is moved into the magnetic resonance system 5. The high homogeneity of the basic magnetic field that is required for the nuclear magnetic resonance measurement is defined in a typically spherical measurement volume M into which the parts of the human body that are to be examined are introduced. To support the homogeneity requirements, and in particular to eliminate temporally variable influences, known as shim plates made of ferromagnetic material are mounted at a suitable point. Temporally variable influences are eliminated via shim coils 2 and a suitable controller 27 for the shim coils 2.

A cylindrical gradient coil system 3 that has three sub-windings is used in the basic field magnet 1. Each sub-winding is supplied by a corresponding amplifier 24-26 with current to generate a linear gradient field in the respective direction of a Cartesian coordinate system. The first sub-winding of the gradient field system 3 thereby generates a gradient $G_x$ in the x-direction; the second sub-winding generates a gradient $G_y$ in the y-direction; and the third sub-winding generates a gradient $G_z$ in the z-direction. The amplifiers 24-26 respectively comprise a digital/analog converter (DAC) which is controlled by a sequence controller 18 for time-accurate generation of gradient pulses.

Located within the gradient field system 3 is a radio-frequency antenna 4 which converts the radio-frequency pulses emitted by a radio-frequency power amplifier into an alternating magnetic field to excite the nuclei and align the nuclear spins of the subject to be examined or, respectively, of the region of the subject that is to be examined. The radio-frequency antenna 4 has one or more RF transmission coils and multiple RF reception coils in the form of an arrangement (annular, linear or matrix-like, for example) of coils. The alternating field emanating from the precessing nuclear spins—i.e. normally the nuclear spin echo signals caused by a pulse sequence made up of one or more radio-frequency pulses and one or more gradient pulses—is also transduced by the RF reception coils of the radio-frequency antenna 4 into a voltage (measurement signal) which is supplied via an amplifier 7 to a radio-frequency reception channel 8, 8' of a radio-frequency system 22. The radio-frequency system 22 furthermore has a transmission channel 9 in which the radio-frequency pulses are generated for the excitation of the nuclear magnetic resonance. The respective radio-frequency pulses are represented digitally in the sequence controller 18 as a series of complex numbers based on a pulse sequence predetermined by the system computer 20. This number series is supplied as real part and imaginary part via respective inputs 12 to a digital/analog converter (DAC) in the radio-frequency system 22, and from this to the transmission channel 9. In the transmission channel 9 the pulse sequences are modulated on a radio-frequency carrier signal whose base frequency corresponds to the resonance frequency of the nuclear spins in the measurement volume. The modulated pulse sequences are supplied to the RF transmission coil of the radio-frequency antenna 4 via an amplifier 28.

The switch-over from transmission operation to reception operation takes place via a transmission/reception diplexer 6. The RF transmission coil of the radio-frequency antenna 4 radiates the radio-frequency pulses into the measurement volume M to excite the spins and samples resulting echo signals via the RF reception coils. The correspondingly acquired nuclear magnetic resonance signals are phase-sensitively demodulated at an intermediate frequency in a first demodulator 8' of the reception channel of the radio-frequency system 22 and are digitized in the analog/digital converter (ADC). This signal is further demodulated to a frequency of zero. The demodulation to a frequency of zero and the separation into real part and imaginary part occur after the digitization in the digital domain in a second demodulator 8 that emits the demodulated data via outputs 11 to an image computer 17. An MR image is reconstructed by the image computer 17 from the measurement data acquired in such a manner. The administration of the measurement data, the image data and the control programs takes place via the system computer 20. Based on a specification with control programs, the sequence controller 18 controls the generation of the respective desired pulse sequences and the corresponding scanning of k-space. In particular, the sequence controller 18 controls the accurately-timed switching of the gradients, the emission of the radio-frequency pulses with defined phase amplitude and base frequency adapted according to the invention, and the reception of the nuclear magnetic resonance signals. The time base for the radio-frequency system 22 and the sequence controller 18 is provided by a synthesizer. The selection of corresponding control programs to generate a series of MR images (which are stored on a DVD 21, for example) as well as other inputs on the part of the user and the presentation of the generated MR images take place via a terminal 13 that has input means (for example a keyboard 15 and/or a mouse 16) to enable an input and display means (a monitor 14, for example) to enable a display. For example, via the input means a user can also select an examination region to be examined (ROI; "region of interest").

Figure 4:
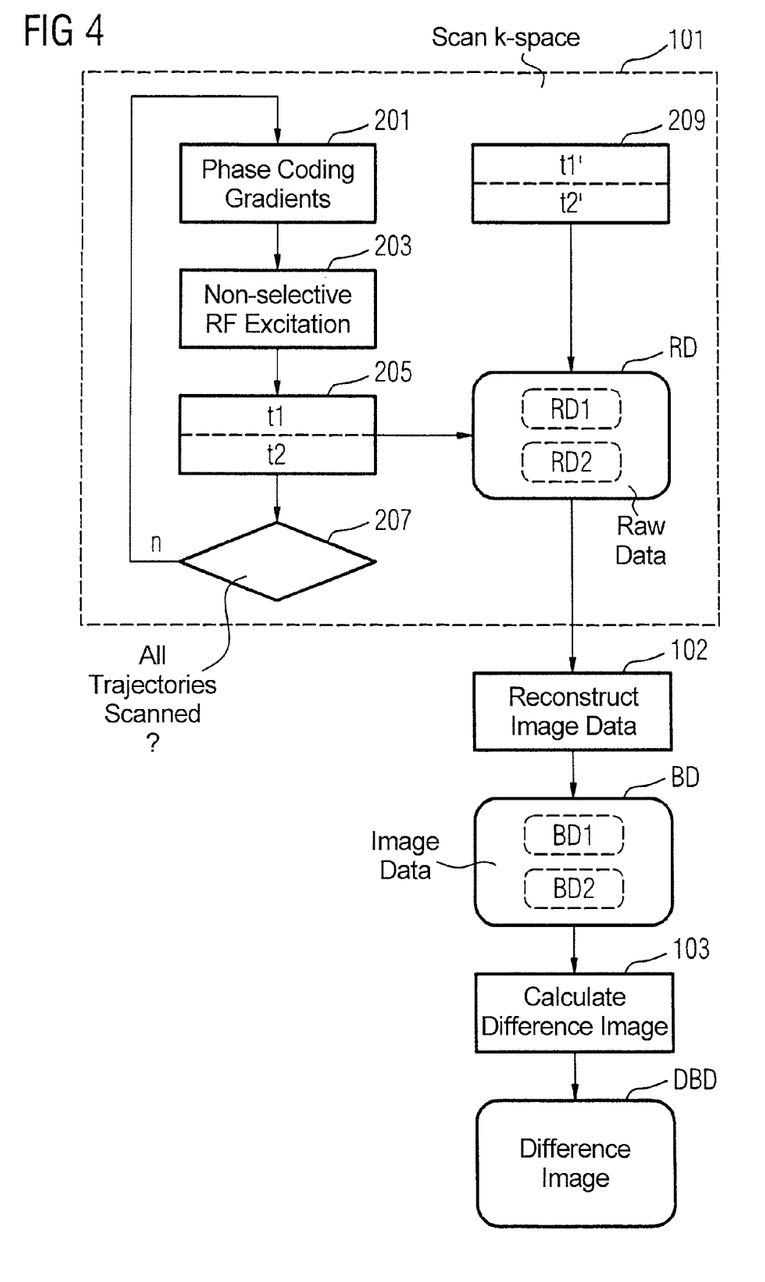
FIG. 4 is a flowchart of an embodiment of a sequence suitable for use in connection with the method according to the invention.

A flowchart of an embodiment of a method according to the invention to create an image data set is schematically depicted in FIG. 4.

In a first Step 101 to create an image data set, k-space corresponding to the examination region to be imaged is hereby read out.

For this at least two phase coding gradients ($G_x$, $G_y$, $G_z$) are switched in a respective spatial direction by means of a gradient system of the magnetic resonance system (Block 201), and a non-slice-selective RF excitation pulse is radiated by means of a radio-frequency antenna of the magnetic resonance system (Block 202). If three phase coding gradients are switched, a three-dimensional image data set can be reconstructed in a conventional manner from the acquired raw data. If only two phase coding gradients are switched, a projection data set can be reconstructed.

After a time t1 after the last radiated excitation pulse, in which the phase coding gradients switched in Block 201 have already reached their full strength, echo signals are acquired by means of the radio-frequency antenna and stored in an evaluation unit of the magnetic resonance system (for example a system computer of the magnetic resonance system) as raw data points RD along the radial k-space trajectory predetermined by the strength of the phase coding gradients.

In one embodiment, echo signals are only acquired after the time t1 and stored as raw data in the raw data set RD. In a further embodiment, after the time t1 after each RF excitation pulse first echo signals are acquired and stored as raw data in a first raw data set RD1, and furthermore after a time t2 after the same RF excitation pulse at least one second echo signal is acquired and stored as an additional raw data point in a second raw data set RD2, wherein t2>t1.

The second echo signal is hereby generated in a known manner, for example via reversing the polarity of the gradients.

After all desired echo signals are acquired after an RF excitation pulse, and therefore after the corresponding k-space trajectory or trajectories has/have been read out, in Step 207 a check is made as to whether k-space corresponding to the imaging area has thus already been read out or not along radial k-space trajectories in a first region (depending on the time t1). If not ("n"), Block 201 is begun again, wherein phase coding gradients differing from the previously used phase coding gradients are switched.

K-space corresponding to the examination region to be imaged and that is not covered by the first region of k-space—which first region is scanned by means of Blocks 201 through 205—is read out at an arbitrary point in time, or also at various points in time before, between or after the readout of the radial k-space trajectories, for example point by point by means of a single point imaging method (RASP, for example) or in another known manner (Block 209), and is likewise stored in the raw data set RD. If the raw data points which include the k-space center are hereby registered in a Cartesian manner, what is known as a regridding before the reconstruction of image data is superfluous.

Given the readout of k-space corresponding to the imaging area, the phase coding gradients can be varied continuously between the radiation of a first RF excitation pulse to acquire raw data points of k-space corresponding to the examination region and a second RF excitation pulse to acquire additional raw data points of k-space corresponding to the imaging area. This means that the phase coding gradients are not ramped down after every acquisition of a radial k-space trajectory and ramped up again for the acquisition of the next k-space trajectory; rather, the phase coding gradients are only ramped up or, respectively, down further from the already assumed strength, until the strength required for the next acquisition is achieved. Eddy currents induced by the current flow of the gradient system that is required to generate the phase coding gradients can thus be reduced, which reduces the formation of noise which is caused by the forces that the eddy currents impinge upon the gradient system.

In particular, it is advantageous to arrange the k-space trajectories to be read out such that the strength of the phase coding gradients must respectively only be varied as slightly as possible, whereby the noises caused by the change of the phase coding gradients can be further reduced in the measurement space M of the magnetic resonance system.

Analogous to the exemplary embodiments already stated above, given the raw data points that are read out by means of a different way (for example by means of single point imaging methods) and which comprise the k-space center, after each RF excitation pulse a raw data point can be read out either only after a first echo time t1' and be stored in the first raw data set RD1; or after a first echo time t1' a first raw data point can be read out and stored in the first raw data set RD1 and after a second echo time t2'—with t1'<t2'—a second raw data point can be read out and stored in the second raw data set RD2. The generation of the second echo thereby takes place again in the known manner.

In a further Step 102, an image data set BD is reconstructed from the acquired raw data points which are stored in the raw data set RD, for example by means of the evaluation device of the magnetic resonance system using a Fourier transformation.

If a first and second raw data set RD1 and RD2 have been acquired and stored, analogously a first image data set BD1 can be reconstructed from the first raw data set RD1 and an additional second image data set BD2 can be reconstructed from the second raw data set RD2.

In a further exemplary embodiment, in the case in which a first and second raw data sets RD1 and RD2 have been acquired and from these a first and an additional, second image data sets BD1 and BD2 have been reconstructed, a difference image DBD can be calculated from this first and second image data sets BD1 and BD2 (Step 103). Via the different echo times t1 and t2 with which the first and second raw data sets RD1 and RD2 have been acquired, from the first and second image data sets BD1 and BD2 it is possible to generate a difference image in which tissue with a predetermined T2 are depicted exclusively.

For example, such a difference image DBD can occur via per-pixel subtraction of the second image data set BD2 from the first image data set BD1 (or vice versa), possibly with a suitable weighting of at least one of the two image data sets BD1 and BD2, for example: DBD=a*BD1−b*BD2, with a and b weighting factors.

The weighting factors a and b are advantageously dependent on a time constant prevailing in the examination region imaged with the image data sets BD1 and BD2, in particular depending on the T2 value prevailing in the examination region. The difference image DBD can therefore be created such that optimally exclusively tissue with a defined (short) T2 is displayed.

Figure 5:
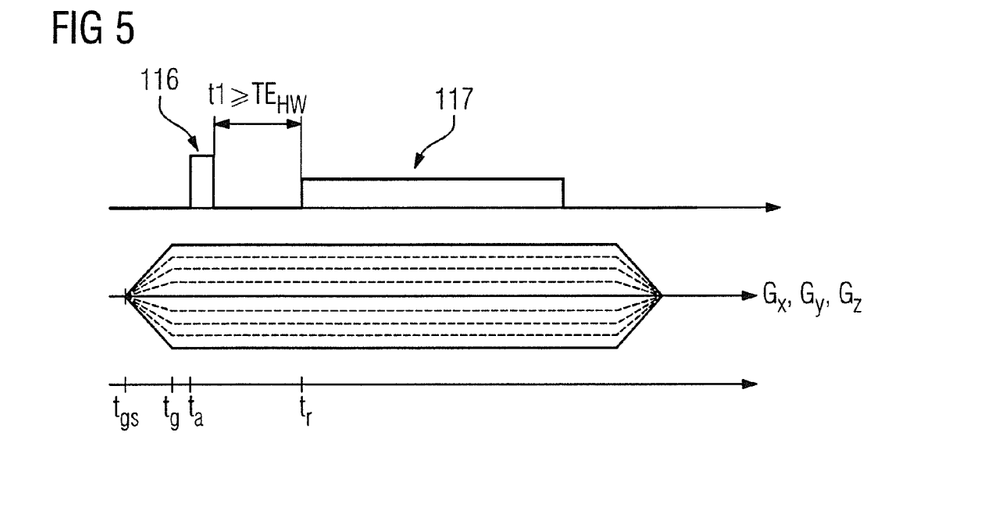
FIG. 5 schematically illustrates a portion of a sequence to acquire multiple raw data points on a radial k-space trajectory suitable for use in connection with the method according to the invention.

The part of a sequence according to the invention that serves to acquire multiple raw data points on a radial k-space trajectory is schematically presented in FIG. 5 (see FIG. 4, Blocks 201-205). At a point in time $t_{gs}$, at least two phase coding gradients $G_x$, $G_y$, $G_z$ are ramped up and reach their full strength at a point in time $t_g$. At a later point in time $t_a > t_g$, an RF excitation pulse 116 is radiated. After an echo time t1 after the RF excitation pulse 116 (that advantageously corresponds to the hardware-dependent minimum switching time between a transmission mode and a reception mode of a radio-frequency antenna $TE_{HW}$ that is used), the readout time period 117 to read out the echo signals is begun at the point in time $t_r$.

In the exemplary embodiment shown in FIG. 5, the phase coding gradients are switched before the RF excitation pulse is radiated.

The RF excitation pulses 116 that are used are hereby, for example, square-wave RF excitation pulses 116 and have a duration of less than 20 microseconds. Such RF excitation pulses 116 can have a spectral curve of a sinc function which has a half-width HWB that corresponds to approximately 20% more than the reciprocal value 1/τ of the duration τ of the RF excitation pulse (half-width HWB≈1.2/τ).

According to the invention, the base frequency of the radiated RF excitation pulses 116 is adapted to the respective simultaneously switched gradients $G_x$, $G_y$, $G_z$. This means that the base frequency of each RF excitation pulse radiated in the sequence that is used is dynamically changed for each RF excitation pulse in the course of the sequence. This is schematically presented in FIG. 6.

Figure 6:
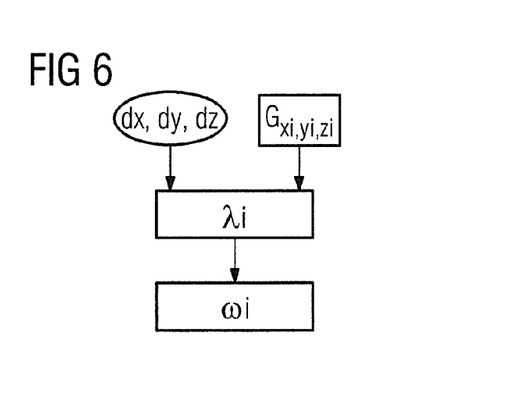
FIG. 6 is a flowchart of an adaptation of RF excitation pulses according to the invention.

According to the prior art, the base frequency of each RF excitation pulse at each repetition of the sequence that is used would amount to $\omega_0 = \gamma B_0$, with γ the gyromagnetic ratio and $B_0$ the basic magnetic field.

According to the invention, the base frequency $\omega_i$ of the i-th RF excitation pulse of the sequence that is used is determined depending on the gradient $G_{xi,yi,zi}$ that is switched at the point in time of the radiation of the RF excitation pulse. In particular given off-center measurements, the base frequency $\omega_i$ of the i-th RF excitation pulse of the sequence that is used is more precisely dependent on the gradient $G_{xi,yi,zi}$, switched at the point in time of the radiation of the RF excitation pulse, at the location dx, dy, dz, which corresponds to the center of an examination region (ROI) to be imaged.

Ideally, the base frequency $\omega_i$ of the i-th RF excitation pulse of the sequence that is used is determined such that it corresponds to the Larmor frequency $\lambda_i$ in the center of the (off-center) examination region (ROI). This is different at every excitation i due to the changing gradients. It thus applies that: $\omega_i = \gamma B_0 + \gamma(G_{xi}dx + G_{yi}dy + G_{zi}dz)$. The phase can also correspondingly be adapted to the gradients that are switched at the same time. For the phase $\phi_i$ of the excitation i it then applies that: $\phi_i = 360° \omega_i / \tau$. In this way a uniform excitation of the examination region can be achieved, and therefore an artifact-free MR image can be generated without the gradient strengths having to be varied.

Figure 7:
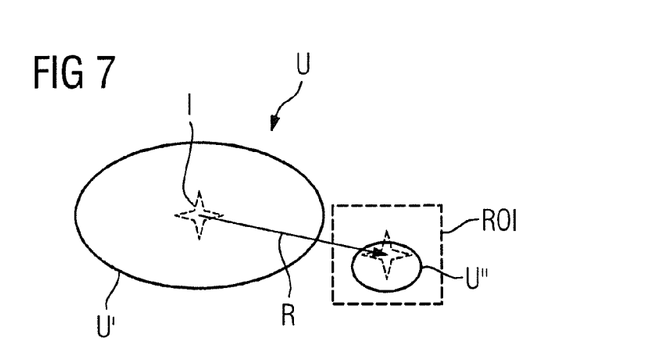
FIG. 7 schematically illustrates an off-center measurement that can be implemented without artifacts with the method according to the invention.

FIG. 7 shows a schematic representation of an off-center measurement as it can be implemented without artifacts with a method according to the invention.

In the presented form, an examination subject U comprises a main part U' in which the center of the measurement volume of the magnetic resonance system (the isocenter I of the magnetic resonance system) is arranged and an adjacent part U'''. The examination region (ROI) to be examined here lies to the side of the isocenter I of the magnetic resonance system and, for example, comprises the adjacent part U''' of the examination subject U. The adjacent part U''' can, for example, be an arm or part of an arm of a patient U. The center of the examination region ROI lies shifted by the vector R (with R=(dx,dy,dz)) from the isocenter I of the magnetic resonance system. With the method according to the invention, even given such an examination region ROI which is arranged "off-center" it is possible to obtain artifact-free MR images of the examination region. The comfort of a patient to be examined is therefore increased since it is no longer necessary to attempt to arranged the examination regions to be examined that are comfortably off-center—for example an arm of a patient—closer to the isocenter of the magnetic resonance system, which frequently leads to uncomfortable positions.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for non-selective excitation of nuclear spin signals in an examination subject in a magnetic resonance (MR) apparatus, comprising:
    placing an examination subject in an MR data acquisition unit and exposing the examination subject to a basic magnetic field in the MR data acquisition unit;
    from a computerized control unit, controlling a scan of the examination subject to acquire MR data therefrom by generating and providing a pulse sequence to the MR data acquisition unit that operates the MR data acquisition unit, with the examination subject therein, to radiate a plurality of non-selective radio-frequency (RF) excitation pulses into the examination subject that each has a base frequency that non-selectively excites nuclear spins in the examination subject and thereby produces MR signals resulting from the excited nuclear spins, while simultaneously activating a phase coding magnetic field gradient that spatially encodes the MR signals, and thereby producing a combined magnetic field in said MR data acquisition unit that is a superimposition of said basic magnetic field and said phase coding magnetic field gradient, said combined magnetic field changing during said scan due to the switching of the phase coding magnetic field gradient; and in said computerized control unit, automatically setting the base frequency of each non-selective RF excitation pulse in said pulse sequence dependent on the combined magnetic field that exists at a time in said pulse sequence at which that respective non-selective RF pulse is radiated, due to the phase coding magnetic field gradient that is simultaneously switched at said time.

2. The method as claimed in claim 1 wherein said examination subject comprises an examination region in which said nuclear spins are excited and from which said magnetic resonance signals emanate, said examination region exhibiting a Larmor frequency that results from said combined magnetic field, and comprising, in said computerized control unit, automatically setting said base frequency of the non-selective RF excitation pulse to said Larmor frequency that results from said combined magnetic field.

3. The method as claimed in claim 1 wherein said RF excitation pulse has a phase, and comprising, in said computerized control unit, also automatically setting said phase of said non-selective RF excitation pulse dependent on said simultaneously switched phase coding magnetic field gradient.

4. The method as claimed in claim 1 wherein said MR data acquisition unit comprises a measurement volume having a center, and comprising radiating said non-selective RF excitation pulse having said adapted base frequency into an examination region of said examination subject that is located outside of said center of said measurement volume.

5. The method as claimed in claim 1 comprising radiating said non-selective RF excitation pulses as square-wave RF excitation pulses.

6. The method as claimed in claim 1 comprising radiating said non-selective RF excitation pulses with a duration of less than 20 microseconds.

7. The method as claimed in claim 1 comprising radiating said non-selective RF excitation pulses with a duration of less than 10 microseconds.

8. The method as claimed in claim 1 comprising radiating said non-selective RF excitation pulses with a duration of less than 5 microseconds.

9. The method as claimed in claim 1 comprising radiating said non-selective RF pulse with said adapted base frequency with a spectral curve that corresponds to a sinc function with a half-width of approximately 20% more than a reciprocal of a duration of said RF excitation pulse with said adapted base frequency.

10. The method as claimed in claim 1 wherein said examination subject comprises an examination region in which said nuclear spins are excited and from which said MR signals emanate, said examination region exhibiting a Larmor frequency that results from said combined magnetic field, and said method comprising, in said computerized control unit, automatically setting said base frequency of each non-selective RF excitation pulse to said Larmor frequency that results from said combined magnetic field.

11. A magnetic resonance (MR) apparatus comprising:

an MR data acquisition unit comprising a radio-frequency (RF) antenna, a gradient coil system, and a basic field magnet that generates a basic magnetic field in said MR data acquisition unit;

a control computer configured to control a scan of the examination subject to acquire MR data therefrom by generating and providing a pulse sequence to the MR data acquisition unit that operates the RF antenna of the MR data acquisition unit, with the examination subject therein, to radiate a plurality of non-selective radio-frequency (RF) excitation pulses into the examination subject that each has a base frequency that non-selectively excites nuclear spins in the examination subject and thereby produces MR signals resulting from the excited nuclear spins, while operating said gradient coil system to simultaneously activate a phase coding magnetic field gradient that spatially encodes the MR signals, and thereby producing a combined magnetic field in said MR data acquisition unit that is a superimposition of said basic magnetic field and said phase coding magnetic field gradient, said combined magnetic field changing during said scan due to the switching of the phase coding magnetic field gradient; and said control computer being configured to automatically set the base frequency of each non-selective RF excitation pulse in said pulse sequence dependent on the combined magnetic field that exists at a time in said pulse sequence at which that respective non-selective RF pulse is radiated, due to the phase coding magnetic field gradient that is simultaneously switched at said time.

12. The MR apparatus of claim 11 wherein said examination subject comprises an examination region in which said nuclear spins are excited and from which said MR signals emanate, said examination region exhibiting a Larmor frequency that results from said combined magnetic field, and wherein said computerized control unit is configured to automatically set said base frequency of each non-selective RF excitation pulse to said Larmor frequency that results from said combined magnetic field.

13. A non-transitory, computer-readable data storage medium encoded with programming instructions, said data storage medium being loaded into a control computer of a magnetic resonance (MR) apparatus that comprises an MR data acquisition unit in which a basic magnetic field is generated, said programming instructions causing said control computer to:

control a scan of the examination subject to acquire MR data therefrom by generating and providing a pulse sequence to the MR data acquisition unit that operates the MR data acquisition unit, with the examination subject therein, to radiate a plurality of non-selective radio-frequency (RF) excitation pulses into the examination subject that each has a base frequency that non-selectively excites nuclear spins in the examination subject and thereby produces MR signals resulting from the excited nuclear spins, and to simultaneously activate a phase coding magnetic field gradient that spatially encodes the MR signals, and thereby producing a combined magnetic field in said MR data acquisition unit that is a superimposition of said basic magnetic field and said phase coding magnetic field gradient, said combined magnetic field changing during said scan due to the switching of the phase coding magnetic field gradient; and automatically set the base frequency of each non-selective RF excitation pulse in said pulse sequence dependent on the combined magnetic field that exists at a time in said pulse sequence at which that respective non-selective RF pulse is radiated, due to the phase coding magnetic field gradient that is simultaneously switched at said time.

14. The storage medium as claimed in claim 13 wherein said examination subject comprises an examination region in which said nuclear spins are excited and from which said MR signals emanate, said examination region exhibiting a Larmor frequency that results from said combined magnetic field, and wherein said programming instructions cause said control computer to automatically set said base frequency of each non-selective RF excitation pulse to said Larmor frequency that results from said combined magnetic field.

\* \* \* \* \*